US010482778B2

(12) United States Patent
Yoo et al.

(10) Patent No.: US 10,482,778 B2
(45) Date of Patent: Nov. 19, 2019

(54) SHAPE AND SIGNAL ADJUSTABLE MOTION SIMULATION SYSTEM

(71) Applicant: Senaptec LLC, Beaverton, OR (US)

(72) Inventors: Herbert Yoo, Beaverton, OR (US); Joseph Bingold, Portland, OR (US)

(73) Assignee: Senaptec LLC, Beaverton, OR (US)

( * ) Notice: Subject to any disclaimer, the term of this patent is extended or adjusted under 35 U.S.C. 154(b) by 196 days.

(21) Appl. No.: 15/400,191

(22) Filed: Jan. 6, 2017

(65) Prior Publication Data

US 2017/0200381 A1 Jul. 13, 2017

Related U.S. Application Data

(60) Provisional application No. 62/275,802, filed on Jan. 7, 2016.

(51) Int. Cl.

| G09B 5/02 | (2006.01) |
|---|---|
| F21S 4/22 | (2016.01) |
| F21S 10/00 | (2006.01) |
| F21V 23/00 | (2015.01) |
| F21V 23/04 | (2006.01) |

(Continued)

(52) U.S. Cl.
CPC ........... *G09B 5/02* (2013.01); *A61B 3/032* (2013.01); *F21S 4/22* (2016.01); *F21S 10/00* (2013.01); *F21V 23/003* (2013.01); *F21V 23/0407* (2013.01); *G09B 9/00* (2013.01); *G09B 19/003* (2013.01); *A61B 3/028* (2013.01); *A61B 3/0325* (2013.01); *A61B 3/08* (2013.01); *A61B 3/09* (2013.01)

(58) Field of Classification Search
CPC .......... G09B 5/02; G09B 9/00; G09B 19/003; F21S 4/22; F21S 10/00; A61B 3/032; F21V 232/003; F21V 232/0407
See application file for complete search history.

(56) References Cited

U.S. PATENT DOCUMENTS

| 4,461,477 A | 7/1984 | Stewart |
| 4,702,475 A | 10/1987 | Elstein et al. |

(Continued)

FOREIGN PATENT DOCUMENTS

| EP | 2 606 815 A1 | 6/2013 |
| KR | 10-20100121143 | 11/2010 |

OTHER PUBLICATIONS

Extended Search Report in corresponding European Application No. 17150608.2, dated May 9, 2017, 7 pages.

(Continued)

*Primary Examiner* — Corbett B Coburn
(74) *Attorney, Agent, or Firm* — Dascenzo Intellectual Property Law, P.C.

(57) ABSTRACT

A device that simulates motion used for training and testing accommodation, vergence, and dynamic visual acuity is provided. The device includes an apparatus having plurality of light sources that can be adjusted in color and luminance disposed on a flexible substrate that can be adjusted to adjust the path and signal to simulate motion of an object. The device can include a controller that includes a processor to provide pre-determined, customizable, or random timing, location, and sequence of the motion presentation. The user response to the simulated motion can be collected, processed, and transmitted by the controller.

31 Claims, 8 Drawing Sheets

(51) Int. Cl.
*G09B 19/00* (2006.01)
*A61B 3/032* (2006.01)
*G09B 9/00* (2006.01)
*A61B 3/028* (2006.01)
*A61B 3/08* (2006.01)
*A61B 3/09* (2006.01)

(56) References Cited

U.S. PATENT DOCUMENTS

| | | | |
|---|---|---|---|
| 4,824,237 A | 4/1989 | Ratner et al. |
| 5,478,239 A | 12/1995 | Fuerst et al. |
| 5,855,425 A | 1/1999 | Hamagishi |
| 7,326,060 B2 | 2/2008 | Seiller et al. |
| 7,651,224 B2 | 1/2010 | Wood et al. |
| 7,828,434 B2 | 11/2010 | Coulter et al. |
| 8,020,992 B2 | 9/2011 | Zhang et al. |
| 8,100,532 B2 | 1/2012 | Yoo et al. |
| 8,197,065 B2 | 6/2012 | Yoo et al. |
| 8,342,685 B2 | 1/2013 | Yoo et al. |
| 8,430,547 B2 | 4/2013 | Reichow et al. |
| 8,485,661 B2 | 7/2013 | Yoo et al. |
| 8,491,119 B2 | 7/2013 | Reichow et al. |
| 8,500,275 B2 | 8/2013 | Yoo et al. |
| 8,553,936 B2 | 10/2013 | Fogt |
| 8,585,202 B2 | 11/2013 | Erickson et al. |
| 8,608,313 B2 | 12/2013 | Reichow et al. |
| 8,668,334 B2 | 3/2014 | Krenik |
| 8,696,126 B2 | 4/2014 | Yoo et al. |
| 8,708,484 B2 | 4/2014 | Reichow et al. |
| 8,714,740 B2 | 5/2014 | Reichow et al. |
| 8,939,769 B2 | 1/2015 | Yoo et al. |
| 8,955,974 B2 | 2/2015 | Gross et al. |
| 8,985,765 B2 | 3/2015 | Reiechow et al. |
| 9,164,221 B2 | 10/2015 | Akutsu et al. |
| 9,457,253 B1 | 10/2016 | Rodriguez |
| 2008/0309616 A1 | 12/2008 | Massengill |
| 2010/0060983 A1 | 3/2010 | Wu et al. |
| 2013/0021811 A1* | 1/2013 | Goldwater ........ B62J 6/00 362/473 |
| 2013/0188127 A1 | 7/2013 | Guillen et al. |
| 2014/0184550 A1 | 7/2014 | Hennessey et al. |
| 2015/0146167 A1 | 5/2015 | Lange et al. |
| 2016/0103339 A1 | 4/2016 | White et al. |
| 2016/0238352 A1* | 8/2016 | Baldridge ........ F41J 5/041 |
| 2016/0262608 A1 | 9/2016 | Krueger |

OTHER PUBLICATIONS

Communication Pursuant to Article 94(3) EPC dated Jun. 8, 2018 (4 pages) from Examination Division out of corresponding EP Application 17150608.2.
Screen Shot—2012 YouTube video located at https://www.youtube.com/watch?v=DNCVSiDbRBY, published 2012.

\* cited by examiner

SHAPE AND SIGNAL ADJUSTABLE MOTION SIMULATION SYSTEM

This application claims priority to U.S. Provisional Application No. 62/275,802 filed Jan. 7, 2016; the entire contents of which is incorporated herein by reference.

The present disclosure relates to a system and method used to evaluate and/or train an individual's visual, oculomotor, or sensorimotor abilities.

The importance of the ability to see an object in motion for tasks related to sport, driving, or other dynamic activities where one maintains sight on a moving object can be appreciated. The ability to maintain sight on a moving object is related to fixating one's gaze on that object and it utilizes biological functions including (1) accommodation of the eyes to maintain focus on the object, (2) vergence of the two eyes to maintain binocular vision on the object, and (3) movement of the eyeballs to maintain the required accommodation and vergence, often called dynamic visual acuity. A motor response is also often required to complete a task involving tracking an object in motion, such as catching a ball in flight or steering a vehicle away from oncoming traffic. These are critical skills for not only success in sports performance but for everyday life activities.

These skills related to accommodation, vergence, dynamic visual acuity, and sensorimotor response can be tested and trained. However, currently known tools have fixed characteristics that limit the type of motion and the representation of the object in motion. Another deficiency of the known tools is that they typically rely on a manual process, which makes them cumbersome and requires a facilitator to be present for the user to be tested or trained.

SUMMARY

Embodiments include systems and apparatus to provide motion simulation that can be adapted to present different simulated motion paths and representations of an object in motion. The simulation of motion is accomplished by providing an apparatus that includes a plurality of individually addressable and controllable light sources provided on a flexible substrate. For example, each light source can be sequentially activated to simulate a light source moving across the flexible substrate. In another example, non-consecutive light sources can be activated to provide stimuli for dynamic vision, accommodation, and vergence testing and/or training. The color and luminance of each light source can also be controlled to provide the adaptability to change the signal presented to the user.

Each of the plurality of the light sources may be fixed on a flexible substrate that can define a linear path. In addition, the flexible substrate can be adjusted into a desired shape to mimic a motion path, such as a parabolic path of a thrown ball or a deflected path of a bouncing object.

The user responds to the motion simulation through a user interface or user response input and the performance measures are collected and can be processed or can be transmitted for further processing.

A method for testing or training an individual's visual, oculomotor, or sensorimotor abilities is also described. The method can include one or more of providing the individual with an apparatus having a plurality of light sources disposed on a first side of a flexible substrate; providing a user response input device; activating one or more light sources in a temporal manner; receiving an input from the user on the user response input device; processing the input and comparing the input with one or more previous inputs; and, visually displaying results of the processing.

Based on the results, recommend training can be provided, after which the above steps can be repeated. A measure of improvement can be determined.

BRIEF DESCRIPTION OF THE DRAWINGS

Illustrative embodiments of the present invention are described below with reference to the attached drawing figures.

DETAILED DESCRIPTION

Using simulated motion instead of using actual object in motion allows for greater efficiency and consistency for the purposes of testing and/or training specific visual, oculomotor, and sensorimotor skills. Embodiments of the invention provide motion simulation with the ability to adjust the shape or path of the motion and the type of signal of the motion, along with the ability to measure user performance.

Figure 1:
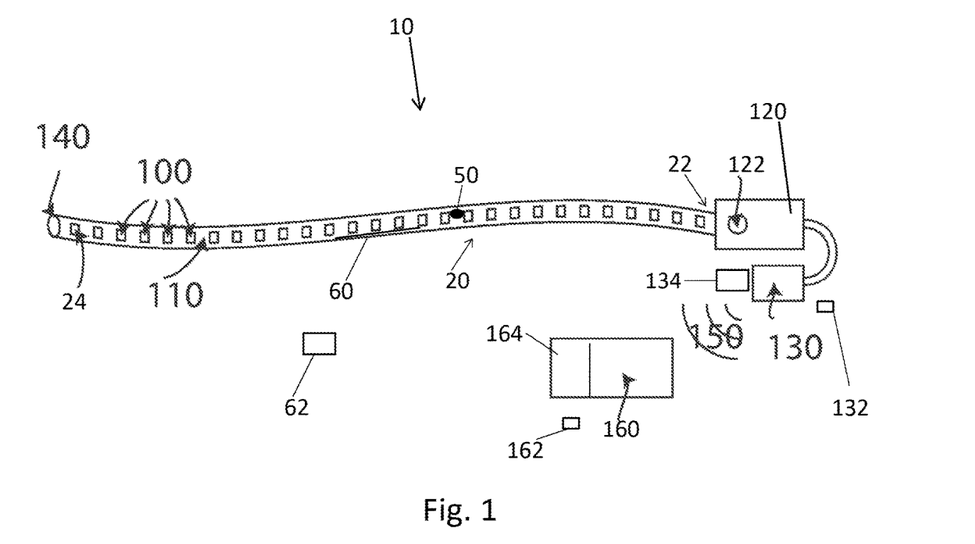
FIG. 1 illustrates an exemplary motion simulating system that shows an apparatus with a shape adjustable substrate for accommodating a plurality of light sources, in accordance with an embodiment of the present invention.

Turning now to the figures, FIG. 1 schematically shows one example of the system 10 according to the present invention. The system 10 includes an apparatus 20, an actuator 120, a controller 130, and optionally or additionally a computing device 160. The apparatus 20 includes a plurality of light sources 100 disposed on a flexible substrate 110. The apparatus 20 may also include an RFID reader 60 that can receive information from an RFID tag 62, which can provide real-time analytical information such as a pace for runners.

Figure 4:
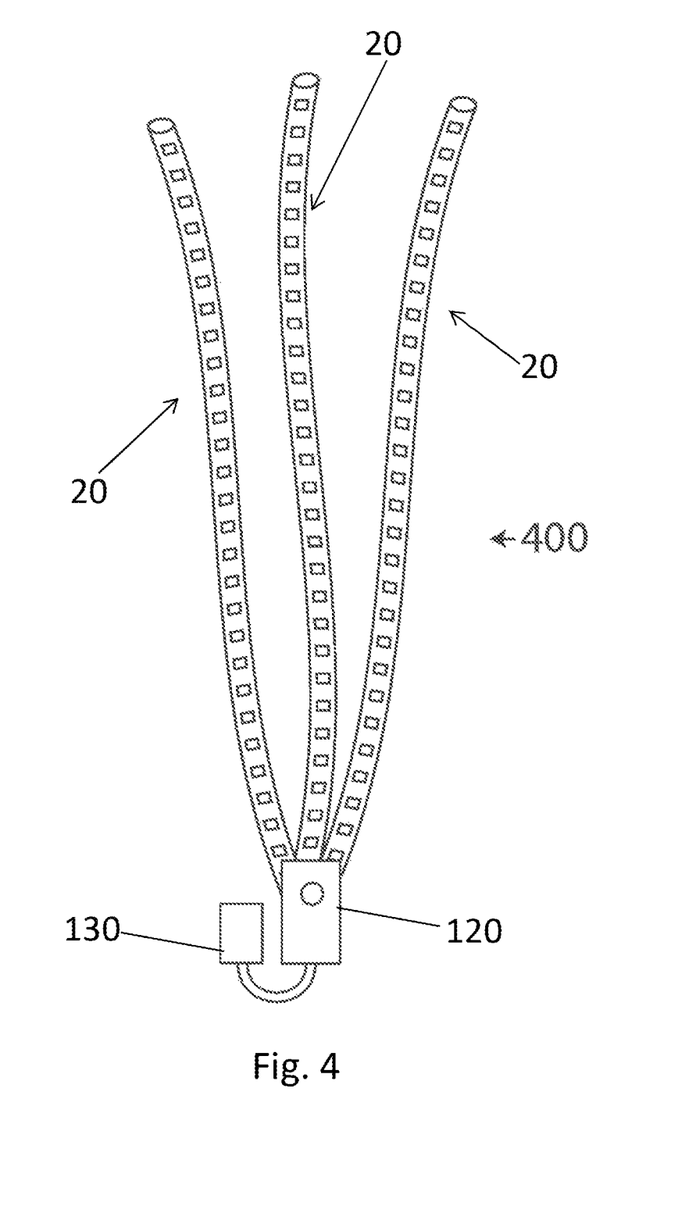
FIG. 4 illustrates the grouping of two or more of the apparatus to provide multiple paths of motion that can be presented concurrently or non-concurrently.

The apparatus 20 has a first end 22 and a second end 24. The first end 22 is configured to be connected to an actuator 120 that is operable to control each individual light source 100. The second end 24 of one apparatus may be connected to a first end 22 of a second apparatus 20 so several apparatus 20 can be connected one to the other in a "daisy chain" manner. Alternatively, as shown in FIG. 4, the first end 22 of several (in this instance, three) apparatus 20 can be individually connected to a single actuator 120.

Each apparatus 20 may have any suitable length such as 1, 2, 3, 4, 5, 6, 7, 8, 9, 10, 11, 12, 13, 14, 15, 16, 17, 18 19, 20, 25, 30, 35, 40 45, 50 or more feet long. One will appreciate that when several individual apparatus 20 are connected together in a daisy chain manner, the total length can be from 50 to 100 or more feet long.

Each light source 100 may emit light upon being activated by the actuator 120. Each light source 100 may include one or more of a florescent light; an incandescent light; a light-emitting diode (LED); an LCD or other type of display; a laser; an electroluminescent light source; a chemical light; a halogen light; or a flexible light wire. Generally, each light source 100 may be any light source that can produce a pulse/flash light effect when electrically controlled by the actuator 120.

The appropriate light source 100 may include a mirror or mirrors (not shown), a globe (not shown), or other devices (many of which are known) so the emitted light will be visible to the user 70 over a range of 180° or in some cases over a range of 360°.

In addition, each light source 100 may be configured to emit light at different frequencies so each light source 100 can emit more than a single color. For example, the light source 100 may be configured to emit white, red, yellow, green, blue, indigo, violet, and combinations of those colors such as orange and the like. It is contemplated that, in use, different colors may require a different response from the individual.

Each light source 100 may be configured so its luminance can be modulated. In other words, each light source 100 may be configured to that upon activation its luminance may be preset (e.g., bright) or it luminance may be modulated during use.

Typically, although not required, each light source is uniformly spaced from one another. For example, each light source may be spaced a distance from about 1 cm, to about 2, 3, 4, 5, 6, 7, 8, 9, 10, 20, 30, 40, 50, 60, 70, 80, 90 or about 100 cm apart.

In an exemplary embodiment, each light source 100 is configured to individually alternate between an active condition (where light is emitted) and an idle condition (where no light is emitted). The active condition may include a state where light is emitted and, while light is emitted, its luminance is modulated.

Typically, the active condition is invoked by the actuator 120 electrically triggering a selected light source 100, from the plurality of light sources 100, to emit light. Electrical triggering may be accomplished by providing a signal to a power supply to supply electricity to the selected light source, providing electricity directly to the selected light source, controlling a switch at the selected light source, or any other method for activating a light source know to those having ordinary skill in the relevant field. The idle condition is invoked by withholding power from the selected light source, causing the selected light source to cease emitting light.

The actuator 120 may include a user response input in the form of a manually operable button 122 with a built-in light source that may also be considered a part of the plurality of light sources 100, although this is unnecessary.

The flexible substrate 110 can be formed of any suitable material that permits the apparatus to be formed in a desired shape and once shaped; the apparatus retains its shape. Suitable flexible substrates 110 include polymers, co-polymers, tri-polymers, block polymers, polymers including rubber and/or butadiene, shape-memory polymers, metals and metal alloys. In one example, the flexible substrate may include a metal wire of a suitable gauge (e.g., 18 gauge), which can be bent or formed into a desired shape and once shaped will retain its shape.

A clear protective casing 140 may be provided to simultaneously surround all the light sources 100 and the flexible substrate 110. Alternatively, the casing 140 may surround only the light sources or may be arranged to surround each individual light source. The casing protects the light sources from physical damage yet allows light to pass through for the user to see the light signals. One will appreciate that the casing is not essential and need not be present.

According to one embodiment, the apparatus 20 may be formed by arranging a number of light sources 100 in an electrically connected manner on a flexible substrate 110 such as a metal wire and providing a clear protective casing 140 (such as a shrink wrap plastic material) around the light sources 100 and flexible substrate 110.

A controller 130 may be configured to interact with the actuator 120 for activating one or more of the plurality of light sources in a temporal manner to create the appearance of movement of light and to control the color and luminance of each light source 100.

Each of the actuator 120 and controller 130 may include a processor that performs or directs functions according to computer code or machine-useable instructions (e.g., test instructions), including computer-executable instructions such as program components, being executed by a computing device (e.g., control unit, input device, or recording device) or other logic-processing machine, such as a personal data assistant, smartphone, or other handheld device. Generally, program components including routines, programs, objects, components, data structures, and the like, refer to code that performs particular tasks, or implement particular abstract data types. Embodiments of the present invention may be practiced in many system configurations, including hand-held devices, consumer electronics, general-purpose computers, specialty computing devices, etc.

Generally, the controller 130 is configured to provide for testing and/or training of the reactionary ability of the user 70. The controller 130 may also be configured to provide desired stimuli (e.g., strobing or pulsing) to the user 70. It will be understood and appreciated by those of ordinary skill in the art that the controller 130 is merely an example of one suitable computing device (computer, smartphone, remote controller) and is not intended to suggest any limitation on the scope of use or functionality of embodiments of the present invention. Accordingly, the controller 130 may take the form of various types of processors commonly deployed in a personal computing device, a handheld device, a tablet PC, a smartphone, a consumer electronic device, and the like. It should be noted, however, that embodiments of the present invention are not limited to implementation on any particular processing components.

In an exemplary embodiment, the controller 130 is generally configured to be any type of microprocessor capable of executing test instructions. By way of example only and not limitation, executing test instructions may include activating one or more of the plurality of light sources 100 in a temporal pattern. The controller 130 may also control any additional visual characteristics, such as color, luminance, orientation, rotation, trajectory, etc., (if present in a given embodiment). In one instance, activating in a temporal pattern may involve, but is not limited to, the following process: selecting a light source of the plurality of light sources 100, electrically triggering the selected light source to cycle to the active condition, maintaining the light source in a the active condition for a predetermined amount of time (e.g., millisecond to minutes), and deactivating the selected light source by returning it to the idle condition. Generally, the process is repeated numerous times as the control unit 130 selects the same or other light sources 100 to cycle through the active condition.

Although electrically triggering is described as activating a selected light source 100 individually, electrically triggering may be practiced by activating more than one light source 100 in conjunction (e.g., simultaneously, in an overlapping manner, additively).

In another instance, activating in a temporal pattern may involve recursively selecting light sources 100 and activating the selected light sources 100 in a sequential manner. As such, "sequential activation" causes one or more light sources 100 of the plurality of light sources 100 to cycle through the active condition individually in an order that simulates motion.

Typically, the scheme of the sequential activation, which influences how motion is simulated, is provided to the controller 130 as test instructions. Generally, as used herein, the phrase "test instructions" is not meant to be limiting but may embrace all types of code, rules, heuristics, logic, etc., that govern such aspects as which light sources to select, the predetermined time of remaining in the active condition, and generally which temporal pattern to follow when sequentially activating the plurality of light sources 100. So upon executing the test instructions, the controller 130 can control the light emitted (including the color of the light) and the luminance from each of the plurality of light sources 100. The test instructions may, for example, be generated by controller 130 in response to parameters entered by a user, such as a coach, physician, trainer, or other individual, or randomly or pseudo-randomly generated by controller 130. Parameters may be, for example, visual traits possessed by the generated light (particularly if the lights are indicia displayed on LCDs or other display devices).

Typically, a power source (not shown) may be electrically connected to the actuator 120 and/or the plurality of light sources 100. As such, the power source assists in supporting operation of some or all of the electrically-driven components. In embodiments, the power source may be a battery, electrical outlet, power cell, solar panel, or any other source of consistent electrical current. In one instance, an electrical current provided from the power source is controlled by the controller 130 and conveyed to the plurality of light sources 100 through the actuator 120.

The processor for the controller 130 may receive instructions from an input device 132. The controller may also include a display 134 suitable for displaying input instructions and/or results obtained when using the system 10 according to methods described below.

The input device 132 and display 134 may be formed as a single unit in the form of a touch-sensitive screen that may be capable of receiving one or more responses as a touch input. A touch-sensitive screen may be any device that may receive touch-based responses. The present invention is not limited to implementation of touch-sensitive screen input device, but may be implemented on any of a variety of types of input devices within the described scope of embodiments. The touch-sensitive screen and display device may comprise a single device that both displays information and receives inputs.

If an input device is touch-sensitive screen, any type of touch-sensitive screen may be utilized. Also, an overlay of a touch-sensitive material may receive touch inputs in conjunction with a display that is not itself touch-sensitive. Such an overlay may be any distance from the display.

More than one input device, such as a touch-sensitive screen, may be used with the system. An alternative input device or devices may comprise, for example, a mouse or scrolling device, microphone, joystick, game pad, keyboard, keypad, game controller, gesture recognition system, and/or any other input-initiating component that may provide wired or wireless data to an input device. An input device may also or alternatively comprise voice recognition equipment and/or software that process auditory inputs.

The display 134 may be capable of displaying information as output images and/or video visually observable and may be any type of television monitor, including cathode ray tube, liquid crystal display, plasma screen, or any other display type. Also or alternatively, the display 134 may comprise one or more screens upon which images are projected, either from the front or from the rear.

The controller 130 may also receive control information from another device 160 such as a controller or computer either in a wired manner or wirelessly 150 such as by a wireless network, near-field communication, Bluetooth protocol or other known wireless near field communication protocols. The controller 130 may also transmit data or other information to the other device 160.

Motion is simulated by progressively activating one or more light sources 100 along the path of the substrate 110. Typically, the light source 100 furthest from the actuator 120 (i.e., the light source 100 adjacent the second end 24) is activated and then, each successive light source is sequentially activated. The user then responds by pressing a user response input. The user response input can take many forms.

In one example, the user response input is shown as a button 122 on the actuator 120. When the light reaches the light source built into the button 122, the user contacts the button to generate a response input. This measurement is called coincidence timing or anticipation timing. The time difference between when the user contacts the button 122 and when the button light source 122 is actually illuminated is the performance measure, which is defined in seconds, milliseconds, etc.

The button 122 is just one embodiment of a user response input. And, while the button 122 is shown as being provided on or as part of the actuator 120, it is contemplated that the button 122 can be provided separate from the actuator and, as is evident from the following description, the button 122 is simply one embodiment of a user response input.

The user response input 50 may include a touch sensor formed as part of any one of or all of the light sources 100 or may include a touch sensor adjacent some or each light source 100. Alternatively, the touch sensor may be provided directly as part of the light source 100. For example, a portion of the light source 100 or any portion of a covering or globe that surrounds each, some, or all of the light sources 100 may be provided with a touch sensor to function as the user response input 50. Other user response inputs 50 could include breaking a light beam, pressing a foot switch, providing a voice response, an accelerometer, or in conjunction with other present or future technologies.

The user response input 50 may include the touch-sensitive screen described above or it may include a different touch screen (not shown). Alternative user response inputs may include, for example, a microphone, joystick, game pad, keyboard, keypad, game controller, gesture recognition system, and/or any other input-initiating component with at least binary distinguishing capabilities that may provide wired or wireless data to an input device in response to the motion simulation information displayed.

A user response input device may also or alternatively comprise voice recognition equipment and/or software to process auditory inputs from a user. For example, the auditory input from the user, to show recognition of the visual indicia, may be a verbalization of the certain characteristics.

If a user response input device is a gesture recognition system, a variety of systems and/or methods may be used to receive inputs. For example, one or more cameras may monitor the movement of a user's body limbs and/or extremities and, in conjunction with appropriate hardware and/or software, register a user response input when the user 70 makes an appropriate gesture. Gesture recognition systems may also use optical markers attached to the user 70 to facilitate motion tracking. Transmitters attached to the subject and receivers (for example, utilizing radio infrared, sonic, subsonic, or ultrasonic transmissions) may also be part of a gesture recognition system.

If the user response input is an eye tracking system, the position and/or focus of the eyes of subject may be monitored and a user response input may be registered when the user's eyes are positioned and/or focused at the proper location.

The user response input 50 may also mimic the equipment used in any activity of interest for the user 70 participating in the testing/training using the system 10. For example, a baseball bat may be swung by the user 70 when the user believes the activated light source (such as, but not limited to, an indicia depicting a baseball displayed on a light sources comprising LCDs) reaches a predetermined location. Similarly, tennis rackets, baseball gloves, hockey sticks (field or ice), lacrosse sticks, croquet mallets, or any other equipment used in an activity, particularly sports, may be used. Inertial sensors may be used in conjunction with actual or simulated equipment. Any other detection method may be used, however, such as motion tracking systems of any kind, detectors that activate when a beam (such as a laser) is interrupted, proximity detectors, and the like.

The user response input 50 may include a vibration sensor provided as part of a tee for use when the user hits a ball (e.g. baseball, softball, etc.) off the tee at the appropriate time based on viewing one or more light sources 100 according to the principles described in this application. This user response input 50 in the form of a sensor can detect when the ball leaves the tee and can then transmit that signal to the controller 130, computer 160, or network 180.

The user response input 50 may also include a vibration sensor incorporated into a foam or soft rubber pad upon which the user 70 may step at the appropriate time. This user response input 50 in the form of a sensor can detect when the user contacts the pad and can then transmit that signal to the controller 130, computer 160, or network 180.

Further, a secondary or other additional user response input may be provided (not shown). A secondary or other user response input may include, for example, an indication of whether the user 70 believes she/he was "early," "late," or "on time." A secondary or other user response input may also include, for example, an identification of a visual characteristic possessed by indicia, such as orientation, color, rotation, etc.

Figure 2A:
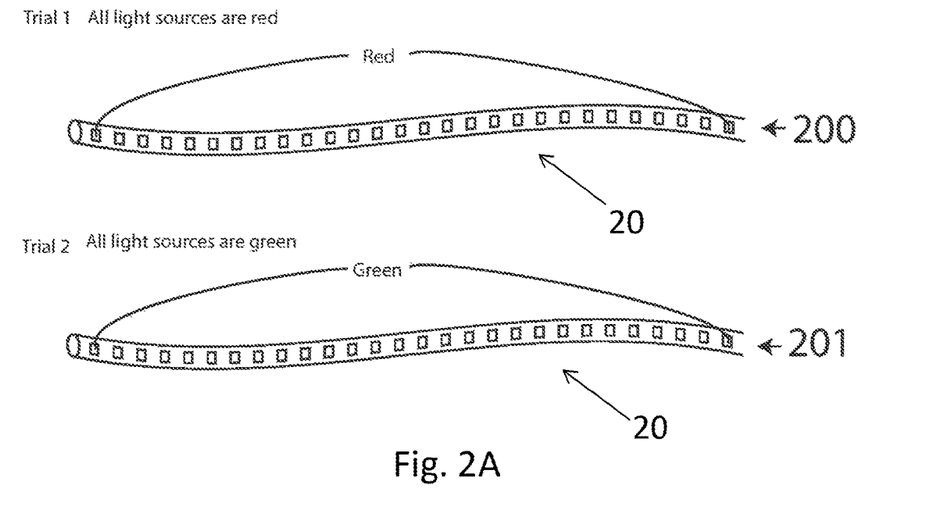
FIG. 2A illustrates how the light sources can be changed in color to adapt the signal presented to the user.

One embodiment of the adjustable aspect of the light sources 100 is shown in FIG. 2A. The motion can be simulated by activating the light sources 100 as red lights in one trial 200 and then activating the light sources as green lights in another trial 201. The user can be instructed to initiate a user response input such as contacting the button 122 or to use another user response input during the green light motion when the green light reaches the button 122, but must not respond when a red motion path is presented. This creates a decision-making demand to the coincidence timing task. Other colors and/or luminance of the light can be used in this method.

Figure 2B:
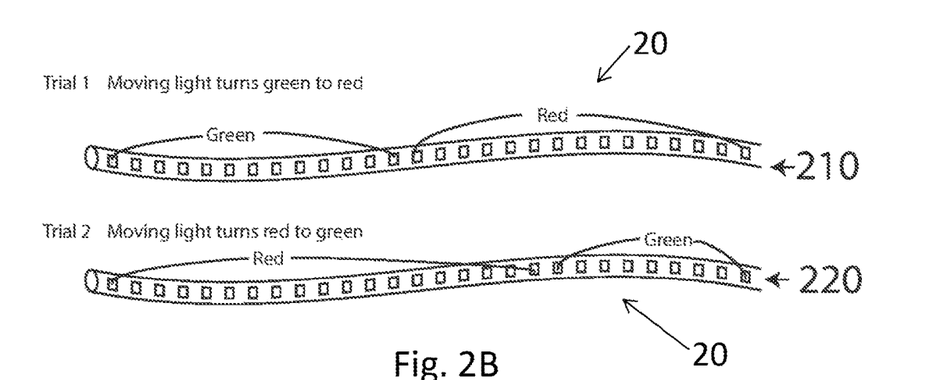
FIG. 2B illustrates how the light sources can be changed in color to adapt the signal presented to the user.

The color or luminance of the signal also can be changed while the light is in motion as illustrated in FIG. 2B. The light in motion could begin as a green light and turn red while it is motion 210 and vice versa 220. The user can be instructed to only initiate a user response input such as contacting the button 122 or another other user response input when the light reaching the button 122 is green and must not respond when the light is red. This creates a response inhibition demand to the coincidence timing task. Other colors and luminance of the light can be used in this method.

Although depicted as a particular temporal pattern, various visually distinct temporal patterns may be expressed by the plurality of light sources, as controlled by the controller 130. These temporal patterns may be expressed when the controller 130 executes one or more test instructions, or may be pre-programmed into the controller 130 or actuator 120. Further, these temporal patterns may include any form of sequential activation of the plurality of light sources 100, which may or may not create the appearance of a light moving. Even further, sequential activation may be any activation that causes one or more light sources 100 to pulse, flash, illuminate for a fixed period of time at a particular color and intensity.

Figure 3A:
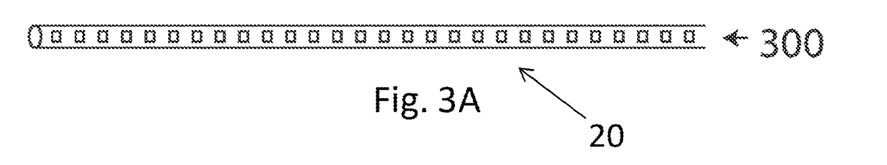
FIGS. 3A-3C illustrate the ability for the apparatus to be changed in shape.
Figure 3B:
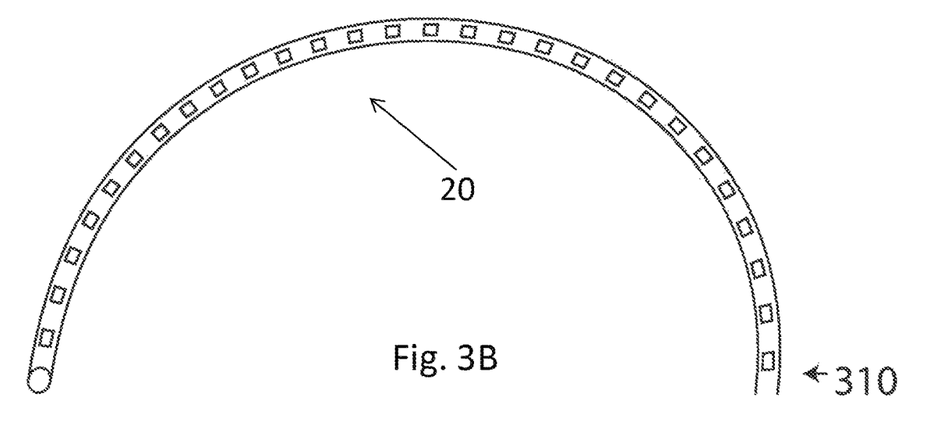
Figure 3C:
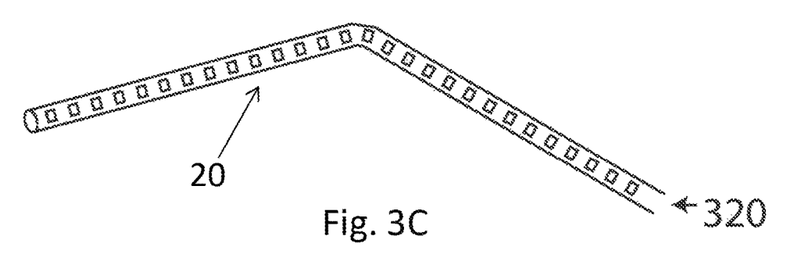

As noted above, the apparatus 20 includes a flexible substrate 110 that can be adjusted to vary the shape of motion as shown in FIGS. 3A-3C. The flexible substrate 110 allows adjustment of the path of motion by bending or flexing the substrate 110 with the plurality of light sources 100. Some, but not all, examples of the paths in FIGS. 3A-3C are linear 300, parabolic or curved 310 to simulate an object thrown in the air, and deflected motion 320 to simulate an object bouncing off a surface. The entire length of the substrate is flexible; therefore an infinite variety of resulting shapes may be produced.

Referring to FIG. 4, two or more of the apparatus 20 can be connected to the actuator 120 to define a group of apparatus 400 to provide multiple paths for motion simulation. The motion can be presented concurrently or non-concurrently among the paths. The controller 130 connected to the actuator 120 can define an activation pattern and timing based on a pre-determined program or can define a random pattern. Similar methods of testing and/or training coincidence timing, decision making, and response inhibition can be utilized.

Figure 5:
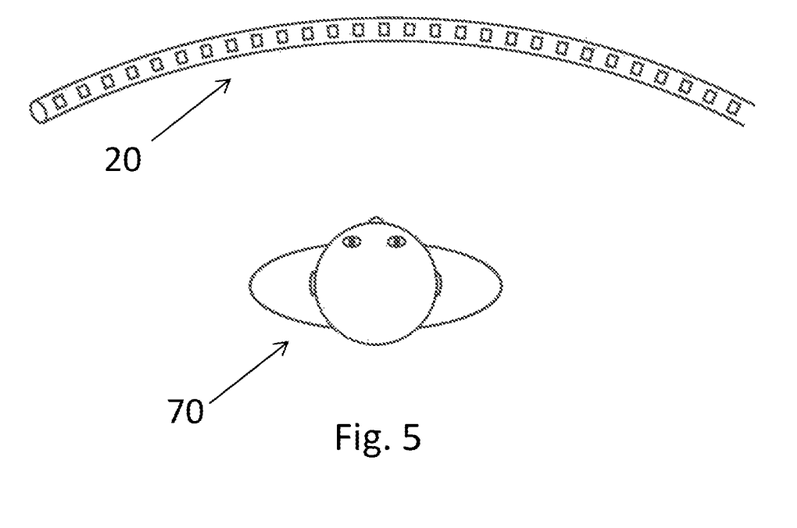
FIG. 5 illustrates a method to use the apparatus for saccadic/pursuit eye movements associated with dynamic visual acuity and visual search.

The light sources can be activated in a non-progressive method to simulate jump-type movements. For example, FIG. 5 shows the apparatus 20 placed at reading distance or farther away from the user 70 where one or more of the light sources 100 would be activated for the user 70 to follow with their eyes. The controller 130 can control the location of the appearance of the light in a random, customized, or pre-defined manner. This presentation provides a method to train saccadic eye movements associated with dynamic visual acuity and visual search.

The light sources 100 can be activated in a progressive method in this orientation to the user 70 to provide simulated motion for testing and training smooth or pursuit eye movements. This type of eye movement is also associated with dynamic visual acuity of following an object in motion or when the user 70 is in motion relative to a fixed object.

The user 70 can either respond with the button 122 on the actuator 120 or with another user response input (e.g., sensor 50) as described above. The activated light source 100 can be adjusted in color so the user 70 only moves their eye fixation only for a certain stimuli and not for another. The colors of the light source 100 can also be used with anaglyphic eyewear to isolate the left or right eye during testing or training.

Figure 6:
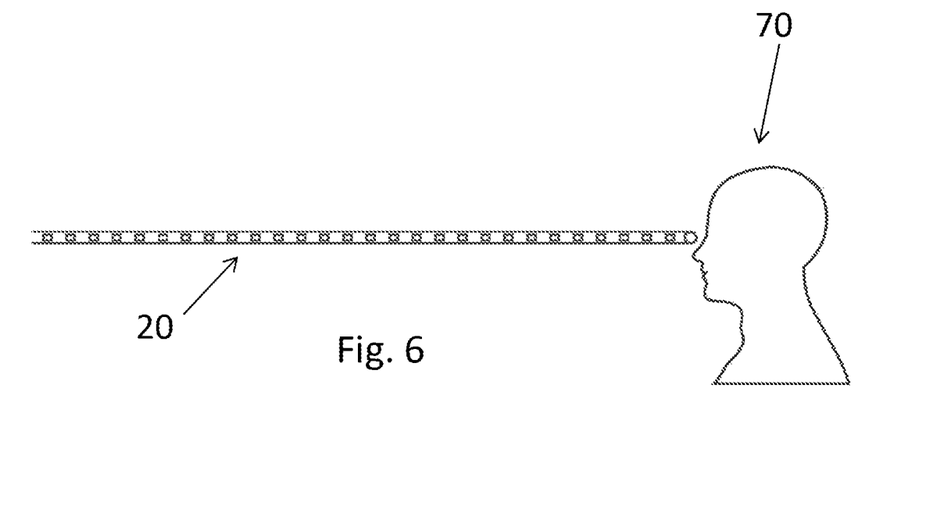
FIG. 6 illustrates a method to use the apparatus for testing and/or training the accommodation and vergence abilities of the user.

When the apparatus 20 is held or positioned close to the eyes of the user 70, as shown in FIG. 6, the system 10 can test or train eye alignment. The controller 130 may control the activation of the light sources 100, which can either be jumping or progressive motion. The user 70 fixes their gaze at the activated light source 100, which requires their accommodation and vergence to be at a certain state. When the activated light source 100 moves to another location, the user 70 moves their gaze to the new location, requiring their accommodation and vergence to be a new state. The color and luminance can be adjusted to provide stimuli to respond and stimuli to not respond. The controller 130 may activate the location and timing of the activation of the light source based on a pre-determined program or in a random fashion.

Figure 7A:
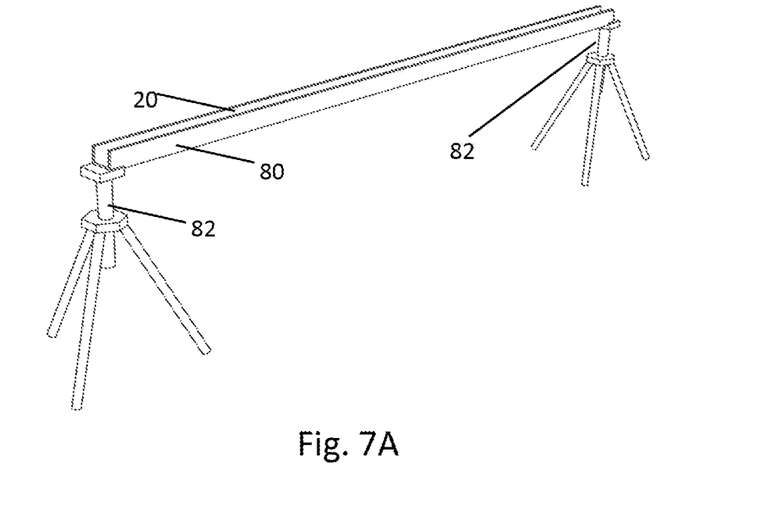
FIG. 7A illustrates an embodiment of the apparatus being supported at a position spaced from a ground surface.
Figure 7B:
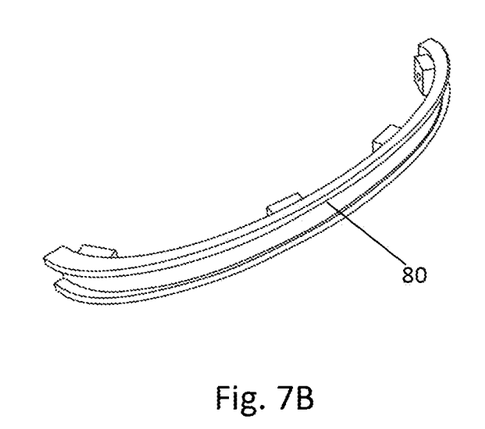
FIG. 7B illustrates an alternative support for the apparatus.

Referring to FIG. 7A is shows an apparatus 20 disposed on a support 80, which in this embodiment has the form of a generally linear u-shaped support. One of skill will appreciate that the support 80 can have any variety of shapes because the flexible substrate 110 can have many shapes. As one example, FIG. 7B shows a support 80 that is curved. In addition, it is unnecessary for the support to be provided with walls; it may simply have a supporting surface on which one side of the flexible support can be supported.

The support 80 can be formed of any suitable material such as metal, plastic, wood, etc. In addition, all or a portion of the support 80 may be translucent or transparent. In certain situations, it may be desirable if the support 80 was completely translucent or transparent. In other situations, it may be desirable if the walls of the support 80, if present, were opaque or such that light does not pass through. Alternatively, the entire support 80 may be opaque.

The support 80 may include one or more height adjustable mounts 82 so the support 80 and thus, the apparatus 20 can be positioned above a ground surface to better simulate flight of an object such as a baseball. It will be appreciated that each of the height adjustable mounts need not be at the same height or distance from the ground. For example, a light source 100 at the farthest distance from the user 70 may be at a height from the ground that is greater than the light source 100 located closest to the user. It will be appreciated that such a difference in height my simulate motion of an object whose height from the ground decreases as it approaches the user (i.e., a sinker ball, slider, etc.).

In view of the above disclosure, it is also apparent that several supports 80 arranged in series may be provided to accommodate several apparatus 20 connected in series (i.e., daisy-chained). It is also apparent that several supports 80 could be arranged to accommodate several apparatus 80 in a manner similar to that shown in FIG. 4, where multiple apparatus 80 are provided adjacent to each other to present to the user 70 multiple simulated paths of travel. In this instance, when multiple apparatus are provided, the system 10 could be operated in a manner such that light sources 100 on a single apparatus 20 light up to present to the user a single path of simulated motion for which the user 70 would react to. It is contemplated that such an operation could be used for training a goalie for a sport like hockey, soccer, lacrosse, etc. By presenting a plurality of paths of simulated travel and requiring the user to make a decision based on a path of travel of the activated light sources 100, the user 70 can be trained to react.

Figure 8:
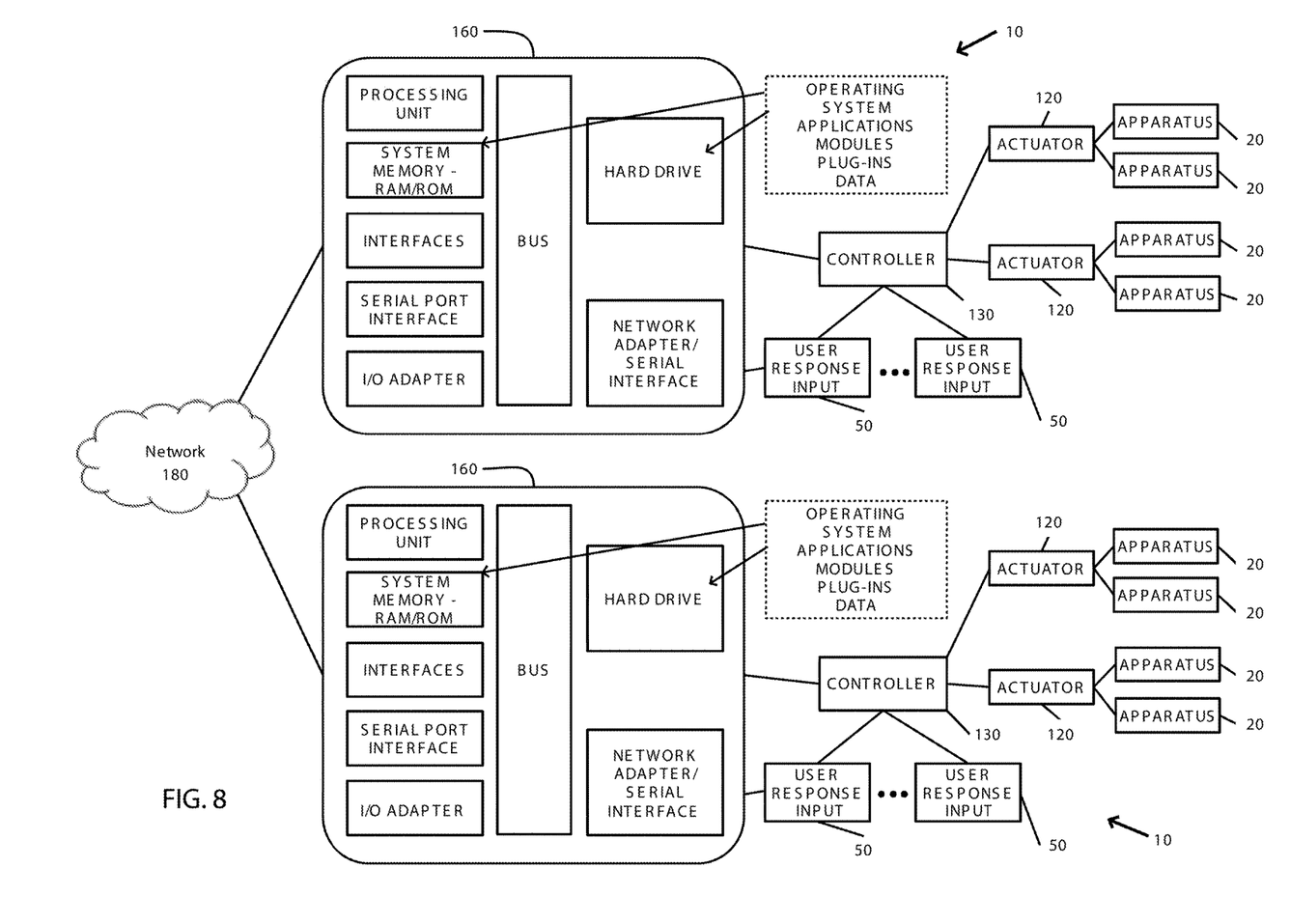
FIG. 8 is a block diagram of a system according to an embodiment of the invention.

As noted above, the activation of the light sources 100, collection of data, and transmission of the data may be controlled directly by the controller 130 or may be controlled through a computing device 160 connected to the controller. Either or both the controller 130 and the computing device 160 may be connected to a network 180 (FIG. 8). The activation pattern may be automated through a pre-defined program that is customizable by the user's sport, position, competition level, or other attributes specific to the user.

All data, including the location and timing of the signal and all response data from the user 70 is gathered. Derivative data such as averages and cumulative scores of the user responses can also be collected, computed and recorded by the controller 130. The controller 130 can further process or store the data. Alternatively or additionally, the controller 130 can receive and transmit the data to another computing device 160 for further processing or storage. Alternatively or additionally, the controller 130 can receive and transmit the data to a network 180 or the computing device 160 may receive and transmit the data to a network 180 for further processing or storage.

As noted above, the communicative connection between the other computer device 160 and the controller 130 may be may be wired or wireless 150. Non-limiting examples of particular wired embodiments include USB connections and cable connections. Non-limiting examples of particular wireless embodiments include a near-range wireless network and radio-frequency technology. It should be understood and appreciated that the designation of "near-range wireless network" is not meant to be limiting, and should be interpreted broadly to include at least these technologies: negotiated wireless peripheral (NWP) devices; short-range wireless air interference networks (e.g., wireless personal area network (wPAN), wireless local area network (wLAN), wireless wide area network (wWAN), Bluetooth™, and the like); wireless peer-to-peer communication (e.g., Ultra Wideband); and any protocol that supports wireless communication of data between devices. And persons familiar with the field of the invention will realize that a near-range wireless network may be practiced by various data-transfer methods (e.g., satellite transmission, telecommunications network, etc.) that differ from the specific illustrated embodiments. Any media or protocol may be used for connection and, accordingly, connection is not further described.

The controller 130 and other computing device 160 may include a display 134, 164, that may be capable of displaying information as output images and/or video visually observable by a user 70 and may be any type of computer, testing apparatus, or television monitor, including cathode ray tube, liquid crystal display, plasma screen, or any other display type. The display may be any type of monitor, display goggles or visor, screen and projector, or other device capable of displaying an image. Also or alternatively, the display may comprise one or more screens upon which images are projected, either from the front or from the rear. Further, the display may provide a subject interface for an administrator to interact with the system 10 before, during, and after use of the system 10.

A database may be configured to store information associated with assessments of users of the system. The information stored in database may be configurable and may include any information relevant to the testing and/or training, such as information describing the location and timing of the signal and response data from the subject, including the accuracy and/or speed of the user's response, Portions or the entirety of database may reside on the controller 130, the other computing device 160, another external computing device (not shown), a network 180, and/or any combination thereof.

The database may be accessed to prepare the system 10 for testing and/or training by providing information relating to the apparatus 20, the user 70, and the type of testing or training.

For example, information relating to the apparatus 20 may include, but is not limited to, the number of apparatus 20 to be controlled, which may include an identifier for each apparatus, the number of light sources 100, the distance between each individual light source, the luminance or desired luminance of each light source.

Information relating to the user 70 may include a username and password, gender, age, physical, or mental condition and other desirable traits.

In some instances, the information relating to the user may include the sport for which the system 10 is being used to train for, the proficiency level of the user (e.g., professional, college or high school player, novice, etc.), the user's position (e.g., goalie, pitcher, catcher, quarterback, receiver, etc.).

The information relating to the user 70 may also include the user's test results; a comparison of a recent test result with historical test results, a comparison of the user's test result or results with a population of other user's using the system 10 for the same type of testing or training. It is contemplated that the comparison of the user's test result or results can be made with a total population of users or any suitable subset.

Information relating to the type of testing or training can include customized testing and training sessions that can be recalled from memory of the computing device 160 or the network 180 and pushed to other users who are using the system 10. The information relating to the type of testing or training can also include created and deployed drills or the creation and deployment of drills. The information may also include instructions and videos on how to use the system 10 for different drills to train different skills.

The information stored in database may also comprise the scores and assessments of other individuals. The scores and assessments of the subject may be used in selecting and/or designing an individualized training program for the user 70, and/or to select a protocol to test the user 70. For example, if a user 70 is scoring well on his assessments, it may be beneficial to test/train him using more advanced and/or difficult tests/training programs. Testing/training may be more difficult in that more information is displayed and/or for less time.

Although not shown, a recording device may be incorporated within the actuator 120, controller 130, and/or other computing device 160. The recording device may be a data-storage component integrated within the controller 130. In operation, the recording device is configured to retain information such as an activation time of the button 120 or other user response input device, an activation time of a predetermined 100 light source, which light source was activated during the activation time, test instructions, test data, and the like. This information may be searchable at the recording device by the controller 130 or other computing device 160. Further, the information may downloadable from the recording device to perform analysis thereof, such as calculating a time period that elapsed between the activation time and the user input response time.

FIG. 8 is a block diagram that illustrates two systems 10 as generally described above, each for evaluating and/or training user's visual, oculomotor, and sensorimotor abilities, and recommending training tasks for the user 70 to improve their visual, oculomotor, and sensorimotor abilities, and being connected to a network so that information and data can be transmitted, to the network 180, stored, processed, and provided to other systems 10 connected to the network 180. Of course, one of skill would understand that any number of systems may be connected to the network.

Specifically, FIG. 8 illustrates a system 10 having an apparatus 20, connected with an actuator 120. It will be appreciated that in one instance, one actuator 120 is connected to one apparatus 20, which is connected to a second apparatus in a serial manner (i.e., daisy chain). And, in another instance, a second actuator 20 is connected to two apparatus in parallel (in a manner shown in FIG. 4, for example). While only two actuators are shown, it should be understood that more than two actuators could be connected to the controller 130. Further, it should be appreciated that more than a single controller 130 may be present in the system 10.

While each actuator 20 is shown connected to the controller 130, it is possible and contemplated that the actuators are connected to the computing device 160 without being connected to the controller.

FIG. 8 also shows two user response inputs 50 that are depicted as being connected to both the controller 130 and the computing device 160. The user response inputs 50 include the button 122 provided on the actuator as well as the user response inputs described above.

The controller 130 is connected to the computing device 160, which contains known processing units, memory, hard drive, interfaces, I/O adapters, and other components, as well as an input device (not shown) and a display (not shown). The computing device is provided in communication with an electronic network 180, such as the Internet.

The computing device 160 (and in some embodiments, the controller 130) may include any type or combination of computing systems, such as handheld devices, personal computers, servers, clustered computing machines, and/or cloud computing systems. In one embodiment, the computing device 160 (and in some embodiments, the controller 130) may be an assembly of hardware, including a memory, a central processing unit ("CPU"), and/or optionally a user interface. The memory may include any type of RAM or ROM embodied in a physical storage medium, such as magnetic storage including a hard disk; semiconductor storage such as solid state disk (SSD) or flash memory; optical disc storage; or magneto-optical disc storage. The CPU may include one or more processors for processing data according to instructions stored in the memory. The functions of the processor may be provided by a single dedicated processor or by a plurality of processors. Moreover, the processor may include, without limitation, digital signal processor (DSP) hardware, or any other hardware capable of executing software.

The user interface or input may include any type or combination of input/output devices, such as a display monitor, touchpad, touchscreen, microphone, camera, keyboard, and/or mouse, as described above. The computing device 160 (and in some embodiments, the controller 130) may be configured to send and receive information from the computing device 160 over the electronic network 180.

Figure 9:
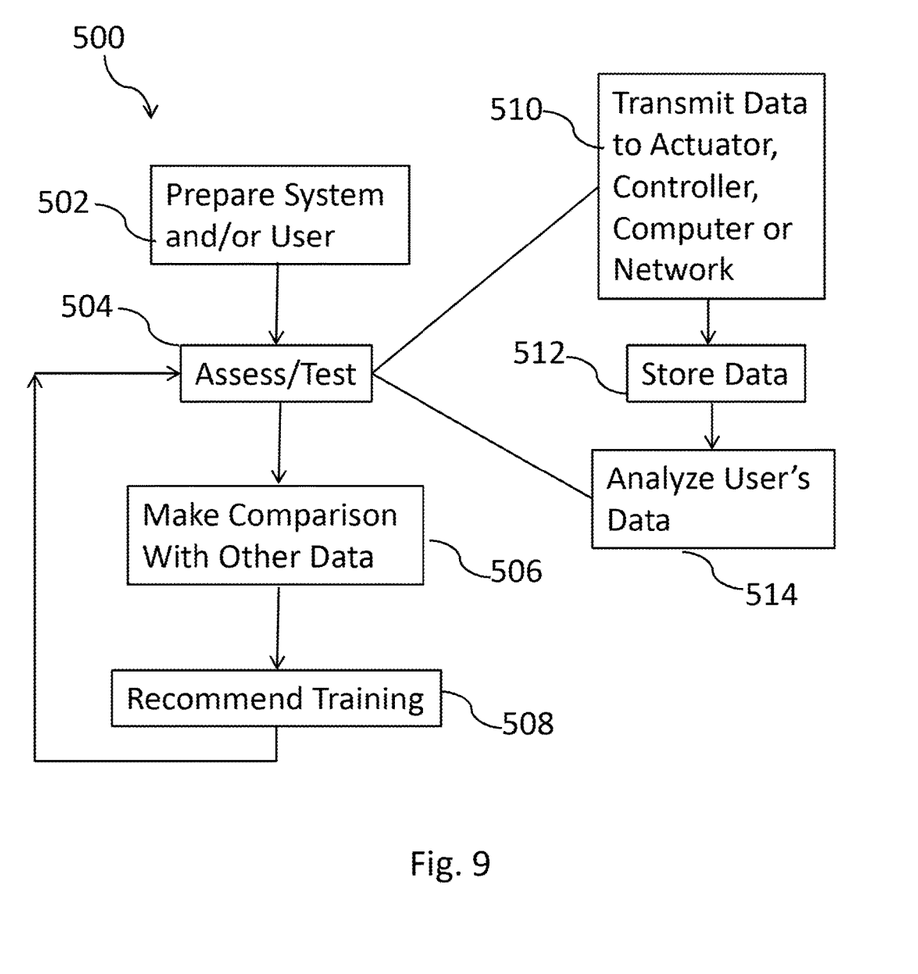
FIG. 9 is a flow diagram of a method for testing and/or training an individual's visual, oculomotor, and/or sensorimotor abilities according to an embodiment of the invention.

Turning now to FIG. 9, a flow diagram of an exemplary method for evaluating and/or training an individual's visual, oculomotor, or sensorimotor abilities is shown. FIG. 9 shows a method 500 that can be performed both by an operator of the system 10 and a user 70, e.g., an individual seeking to improve their visual, oculomotor, or sensorimotor abilities.

The method 500 may include preparing the system 10 and/or user 70 (step 502). The preparation step 502 may include the database to obtain and/or provide information about the system 10 and the user 70 as described above.

The method 500 may then include the assessing and/or testing the user 70 by providing a suitable motion stimulus using the system 10 and apparatus described above. The assessing and/or testing step 504 will also include reassessing and/or retesting, as will become evident.

The assessing and/or testing step 504 may include (a) transmitting the data 510 such as the timing of user response input, data about the activation of particular light sources 100, and any other data to the controller 300, computer 160, and/or network 180 (b) storing the data 512, and (c) analyzing the data 514.

The method 500 may then include making a comparison or comparisons 506 between the analysis of the user's current data and prior analyses of the user's data or between the user's data and data from other users, data from objective sources, or data from any suitable known and useful source to determine or evaluate the user's proficiency.

The method 500 may then include providing recommended training 508 to improve the user's proficiency.

The method 500 may then include reassessing and/or retesting 504.

With the above in mind, it is contemplated that the system 10 and method 500 can be used in the following non-limiting exemplary modes:

Evaluation Mode

This mode is a basic evaluation mode, which can be the same for each user 70. This mode can create a normative database of anticipatory timing characteristics across a multitude of demographics. Suitable measurements and analyses that may be performed can include, but are not limited to overall score, Total error of all trials (summation of absolute value of each error), in both time and distance, average error for all trials in both time and distance, smallest error of all trials in both time and distance, error for each individual trial in both time and distance.

Training Modes

The training mode can include, but are not limited to these modes:
a. an anticipation timing mode,
b. a go-no-go mode,
c. an accommodation/vergence mode
d. a saccadic mode,
e. an Amblyopia mode, and
f. a pace setting mode.
While exemplary modes are noted above, one of skill will appreciate that several modes and/or uses of the apparatus 20 are contemplated and thus, the above modes should not be considered the exclusive or only modes or uses of the system 10 and/or apparatus 20. Further explanation of the above modes follows.

Anticipation Timing Mode

The anticipation timing mode provides simulated motion by progressively activating one or more light sources 100 along the path of the apparatus 20. The activated light source 100 starts at the light source 100 away from the user 70, and moves along the group of light sources toward the user 70. The user 70 then responds by providing a user response input as described above. This may include contacting the button 122 when the light reaches the use. This measurement is called coincidence timing or anticipation timing. The difference between the actual user response input and when the light actually reached the target or user is the performance measurement in time units, which is defined in seconds, milliseconds, etc., which can then be translated into distance (e.g., inches, cm).

Preparing the system may include defining the number of trials to be conducted by the user 70, the speed at which each light source 100 is activated, whether the activation is speed is constant or random, a direction of light travel, the color and/or luminance of the light sources 100, whether the light sources 100 will provide alternating colors or patterns.

Measurements and analyses may include an overall score, a total error of all trials (summation of absolute value of each error), in both time and distance, an average error for all trials in both time and distance, the smallest error of all trials in both time and distance. For each apparatus or system, the error for each user trial in both time and distance. The error may be defined as the difference between where the light is and where the user is (e.g., user response input for inbound motion and end of light string for outbound motion). For example, the error can be quantified as either early (user response input was too soon) or late (user response input was too late).

Go-No-Go Mode

In this mode, the motion can be simulated by activating the light sources 100 as green lights in one trial and then activating the light sources 100 as red lights in another trial, as shown in FIGS. 2A and 2B. The user 70 can be instructed to activate the user response input on the green light motion when it reaches the user, but must not respond when a red motion path is presented. This creates a decision making demand to the coincidence timing task. Other colors and/or luminance of the light can be used in this method.

Preparing the system may include defining the number of trials to be conducted by the user 70, the speed at which each light source 100 is activated, whether the activation is speed is constant or random, a direction of light travel, the color and/or luminance of the light sources 100, whether the light sources 100 will provide alternating colors or patterns, the ratio of Go to No-Go events.

Measurements and analyses may include an overall score, a total error of all Go trials (summation of absolute value of each error), in both time and distance, an average error for all Go trials in both time and distance, the smallest error of all Go trials in both time and distance, for each apparatus or system, the error for each user Go trial in both time and distance. The error may be defined as the difference between where the light is and where the user is (e.g., user for inbound motion and end of light string for outbound motion). For example, the error can be quantified as either early (user response input was too soon) or late (user response input was too late). For each apparatus and for each No-Go trial, whether the No-Go succeeded or not, and how much time was available to decide.

Accommodation/Vergence Mode

This mode is shown in FIG. 6 and is described above.

Saccadic Mode

This mode is shown in FIG. 5 and is described above.

Amblyopia Mode

Amblyopia refers to decreased vision in one or both eyes due to abnormal development of vision in infancy or childhood. In amblyopia, there may not be an obvious problem of the eye. Vision loss occurs because nerve pathways between the brain and the eye aren't properly stimulated. The brain "learns" to see only blurry images with the amblyopic eye even when glasses are used. As a result, the brain favors one eye, usually due to poor vision in the other eye. Another word for amblyopia is often "lazy eye." It is the leading cause of vision loss amongst children.

A common treatment for amblyopia is to put a patch over a dominant eye to force the brain to use the non-dominant eye. Another method is to use color filtered glasses with anaglyphic presentations to force both the dominant and non-dominant eyes to work together by isolating a different image for each eye.

The system 10 and apparatus can be used with color filtered glasses tuned with the color of the light sources 100 to force both eyes to work by isolating what each eye can see. For example, with red/cyan colored glasses, the left eye with a red lens could only see the cyan colored light sources 100 while the right eye with a cyan lens could only see the red colored light sources 100. Advantageously, as the light travels down the path of the apparatus 20, the convergence and accommodation systems are being engaged.

Pace Setting Mode

The system 10 and apparatus may be configured to set a defined pace while the user 70 in motion. The apparatus 20 may be placed adjacent a track, along a race course, or even under water. As such, it can provide real-time pace information while the user 70 is in motion. For example, a user 70 can preset a pace at which the want to run and each or the appropriate light source will be activated to provide an indication of the preset pace.

Further, if the user 70 is provided with an RFID tag 62 and the apparatus 20 is provided with an RFID reader or vice versa, the system 10 can monitor the pace of the athlete and provide real time feedback on their performance.

Strobe or Pulse Mode

The apparatus 20 may be configured such that some or all the light sources 100 are activated at the same time to produce a strobe or pulse effect. As a result, the light sources 100 can be activated at a predefined or random frequency. The apparatus 20 can be used to provide light therapy or can be used with appropriate eyewear to provide electronic or other types of shutters in front of each eye. Such therapy may include therapy for traumatic brain injury, concussions, ADHD, Alzheimer's, stroke, and other conditions.

Vision Therapy

It is also contemplated that the apparatus 20 can be used to provide selected light frequency to the user 70, which might be useful for addressing visual dysfunctions, including strabismus (eye turns), amblyopia (lazy eye), focusing and convergence problems, learning disorders, and the after-effects of stress and trauma.

Vision therapy may also include use of the apparatus 20 to treat EMDR (Eye Movement Desensitization and Reprocessing). Use of the apparatus 20 in this manner may enable the user 70 to heal from symptoms and emotional distress that are the result of disturbing life experiences. Use of EMDR therapy has demonstrated that individuals can experience the benefits of psychotherapy that once took years to make a difference. Known treatment relies on the patient tracking the clinician's hand with their eyes during the therapy session. Use of the system 10 and apparatus 20 can provide a light source that the user 70 can follow and that can be manipulated to follow a path designed by the therapist. Automating the movement permits take home therapy and greater flexibility in the treatment options.

While this invention has been particularly shown and described with reference to preferred embodiments, it will be understood by those skilled in the art that various changes in form and detail may be made without departing from the spirit and scope of the invention. The inventors expect skilled artisans to employ such variations and the inventors intend the invention to be practiced otherwise than as specifically described herein. Accordingly, this invention includes all modifications and equivalents of the subject matter recited in the following claims as permitted by law. Moreover, any combination of the above-described elements in all possible variations thereof is encompassed by the invention unless otherwise indicated or otherwise clearly contradicted by context.

The invention claimed is:

1. A system for training and/or testing an individual's visual, oculomotor, or sensorimotor abilities that comprises:
    an apparatus comprising a plurality of light sources provided on a first side of a flexible substrate;
    an actuator configured to be at least electrically connected to the apparatus to activate each of the plurality of light sources from which light is emitted that is visible to an individual;
    a response input device that receives a response input from the individual, the response input made in response to emitted light from one or more of the plurality of light sources, wherein the response input device comprises a manually operable button; and
    a controller in communication with the actuator and the response input device, wherein the controller controls at least one of a sequence, color, and luminance of each of the plurality of light sources, receives the response input, and electronically collects data in an electronic format for further processing, wherein the plurality of light sources provide a visual impression of a straight or curved path of motion simulation by progressively activating individual lights on the flexible substrate.

2. The system according to claim 1 wherein the controller further comprises an input device and a display, wherein results of the processing are visibly displayed on the display.

3. The system according to claim 1 wherein the controller is in communication with a computer comprising:
    a data storage device that receives input instructions; and
    a processor configured to execute the input instructions to direct the controller.

4. The system according to claim 1, wherein the flexible substrate is elongated.

5. The system according to claim 1, wherein the flexible substrate can be adjusted to simulate a desired motion path.

6. The system according to claim 5, wherein the flexible substrate is adjusted to simulate a) a parabolic path of a thrown object or b) a deflected path of a bounced object.

7. The system according to claim 1, wherein the response input device is continuously in electrical communication with the actuator from a time prior to when the individual applies the response input to the response input device to when the individual applies the response input to the response input device.

8. The system according to claim 1, further comprising a computer device separate from the controller, wherein the computer device receives the data from the controller.

9. A method for testing or training an individual's visual, oculomotor, or sensorimotor abilities comprising:
 providing an individual with an apparatus comprising a plurality of light sources disposed on a first side of a flexible substrate;
 providing a user response input device, wherein the user response input device comprises a manually operable button;
 activating one or more light sources in a temporal manner via an actuator, wherein the plurality of light sources provide a visual impression of a straight or curved path of motion simulation by progressively activating individual lights on the flexible substrate;
 receiving an input from the individual on the user response input device and the receiving the input comprises the individual manually actuating the manually operable button,
 processing the input and comparing the input with one or more previous inputs; and
 visually displaying results of the processing.

10. The method of claim 9 further comprising transmitting the input to a computer comprising a processor configured to compare the input with the one or more previous inputs.

11. The method of claim 10 further comprising visually displaying recommended training based on a comparison of the input with the one more previous inputs.

12. The method according to claim 9, wherein the flexible substrate is elongated.

13. The method according to claim 9, further comprising adjusting the flexible substrate to simulate a desired motion path.

14. The method according to claim 13, wherein the adjusting comprises adjusting the flexible substrate to simulate a) a parabolic path of a thrown object or b) a deflected path of a bounced object.

15. The method according to claim 9, wherein the user response input device is in continuous electrical communication with the actuator from a time prior to when the individual applies the input to the user response input device to a time of receiving the input from the individual on the user response input device.

16. The method according to claim 9, wherein the visually displaying results of the processing is performed on a device that is physically separate from a structure that performs the processing.

17. A system for training and/or testing an individual's visual, oculomotor, or sensorimotor abilities that comprises:
 an apparatus comprising a plurality of light sources provided on a first side of a flexible substrate;
 an actuator configured to be at least electrically connected to the apparatus to activate each of the plurality of light sources from which light is emitted that is visible to an individual;
 a response input device that receives a response input from the individual, the response input made in response to emitted light from one or more of the plurality of light sources, wherein the response input device comprises a touch sensor associated with one of the plurality of light sources; and
 a controller in communication with the actuator and the response input device, wherein the controller controls at least one of a sequence, color, and luminance of each of the plurality of light sources, receives the response input, and electronically collects data in an electronic format for further processing, wherein the plurality of light sources provide a visual impression of a straight or curved path of motion simulation by progressively activating individual lights on the flexible substrate.

18. The system according to claim 17, wherein the controller further comprises an input device and a display to display results of the further processing.

19. The system according to claim 17, wherein the controller is in communication with a computer comprising:
 a data storage device that receives input instructions; and
 a processor configured to execute the input instructions to direct the controller.

20. The system according to claim 17, wherein the flexible substrate is elongated.

21. The system according to claim 17, wherein the flexible substrate can be adjusted to simulate a desired motion path.

22. The system according to claim 21, wherein the flexible substrate is adjusted to simulate a) a parabolic path of a thrown object or b) a deflected path of a bounced object.

23. The system according to claim 17, wherein the response input device is continuously in electrical communication with the actuator from a time prior to when the individual applies the response input to the response input device to when the individual applies the response input to the response input device.

24. A method for testing or training an individual's visual, oculomotor, or sensorimotor abilities comprising:
 providing an individual with an apparatus comprising a plurality of light sources disposed on a first side of a flexible substrate;
 providing a user response input device, wherein the user response input device comprises a touch sensor associated with one of the plurality of light sources;
 activating one or more light sources in a temporal manner via an actuator, wherein the plurality of light sources provide a visual impression of a straight or curved path of motion simulation by progressively activating individual lights on the flexible substrate;
 receiving an input from the individual on the user response input device and the receiving the input comprises the individual manually actuating the touch sensor,
 processing the input and comparing the input with one or more previous inputs; and
 visually displaying results of the processing.

25. The method of claim 24 further comprising transmitting the input to a computer comprising a processor configured to compare the input with the one or more previous inputs.

26. The method of claim 25 further comprising visually displaying recommended training based on the comparing.

27. The method according to claim 24, wherein the flexible substrate is elongated.

28. The method according to claim 24, further comprising adjusting the flexible substrate to simulate a desired motion path.

29. The method according to claim 28, wherein the adjusting comprises adjusting the flexible substrate to simulate a) a parabolic path of a thrown object or b) a deflected path of a bounced object.

30. The method according to claim 24, wherein the user response input device is in continuous electrical communication with the actuator from a time prior to when the individual applies the input to the user response input device to a time of receiving the input from the individual on the user response input device.

31. The method according to claim 24, wherein the visually displaying results of the processing is performed on a device that is physically separate from a structure that performs the processing.

\* \* \* \* \*